United States Patent [19]

Duran

[11] Patent Number: 4,865,046

[45] Date of Patent: Sep. 12, 1989

[54] SERIAL DRAIN COLLECTOR

[76] Inventor: Edna Duran, 15560 Schneider La., New Berlin, Wis. 53151

[21] Appl. No.: 265,017

[22] Filed: Oct. 31, 1988

[51] Int. Cl.$^4$ ............................................... A61B 5/00
[52] U.S. Cl. ................................. 128/762; 128/771; 604/318
[58] Field of Search .............. 128/760, 762, 767, 771; 604/80, 81, 191, 257–260, 317, 318, 319, 322, 326, 403, 404; 222/94, 142.5

[56] References Cited

U.S. PATENT DOCUMENTS

| | | | |
|---|---|---|---|
| 3,194,069 | 7/1965 | Scott | 128/762 |
| 3,345,980 | 10/1967 | Coarda | 128/771 |
| 3,561,427 | 2/1971 | Profy | 128/762 |
| 3,722,502 | 3/1973 | Besumer et al. | 128/762 |
| 3,982,898 | 9/1976 | Mc Donald | 128/762 |
| 4,042,337 | 8/1977 | Griffith | 128/762 |
| 4,241,017 | 12/1980 | Balistreri et al. | 128/760 |
| 4,388,922 | 6/1983 | Telang | 128/760 |

*Primary Examiner*—Max Hindenburg
*Attorney, Agent, or Firm*—Andrus, Sceales, Starke & Sawall

[57] ABSTRACT

A serial urine sample collection device for use in monitoring the color and clarity of successive samples from a patient recovering from surgery includes a unitary container having a plurality of separate serially arranged compartments each having a transparent face. Each compartment is filled by pouring the urine from a single voiding into a top opening and draining any excess through a valve-controlled outlet in the bottom of the compartment to a main storage reservoir disposed below. Visual indicators of various types are provided to help maintain the samples in the compartments in proper chronological sequence so that improvement in color and clarity of the urine with time may be visually monitored. The device improves the accuracy, safety, and convenience of the monitoring procedure, while minimizing sample handling and improving the hygenic nature of the procedure.

19 Claims, 2 Drawing Sheets

SERIAL DRAIN COLLECTOR

BACKGROUND OF THE INVENTION

The present invention relates to a device for the serial collection of body fluids and, more particulary, to a device useful in the post-surgery serial collection and analysis of urine samples.

In certain surgical procedures involving the urinary system, such as resection of the prostate, the patient is initially catherized after surgery with a conventional foley catheter to allow urine and blood clots to be freely drained from the bladder. After a period of days, typically 2-5, the catheter is removed and serial urine specimens from subsequent voidings are visually analyzed to observe urine clarity. As healing progresses and the blood content of the urine samples diminishes or disappears, urine clarity is one of the most significant factors utilized by the physician in determining when the patient can be discharged. After the catheter is removed, it is important that a sample from each voiding be observed and compared with preceeding samples to determine changes in relative clarity.

Presently, serial urine samples are collected by taking a portion of each voiding into a conventional urinal and pouring it into a specimen bottle or jar. A patient who is ambulatory and self-sufficient may be given several specimen bottles and asked to pour a sample from the conventional urinal into a bottle. If the patient is assisted by the nursing staff, the procedure is essentially the same. In either case, the procedure is cumbersome, inconvenient, and relatively unsanitary. In addition, the use of several individual sample bottles can result in a mixup, sample loss by spilling and the like, or other inaccuracies in the monitoring of the serial specimens.

Serial collection of urine from a catheterized patient is well known in the art. U.S. Pat. No. 3,722,502 discloses a urine collection bag within which the outlet end of a catheter may be manually positioned to direct the flow into individual separable compartments or a larger reservoir to handle excess flow. The system is intended particulary to preclude external sample contamination. U.S. Pat. Nos. 3,561,427 and 3,194,069 show devices for the automatic serial collection of urine samples from a catheterized patient, the devices being intended primarily for determining timed urinary output. The device disclosed in each of the patents includes a large cylindrical collection container divided into separate compartments into which the flow is serially directed by automatic timed rotation of the collection container.

U.S. Pat. No. 3,982,898 discloses a device for the collection of urine from a single voiding and dividing it into multiple test samples. The single sample is directed into an upper container where it drains through multiple openings into a compartmented lower container to provide equal volume test samples. U.S. Pat. No. 4,042,337 also shows a device for dividing a single voiding into multiple test samples. The collection apparatus directs the initial forestream portion into a main reservoir and, after receiving a predetermined volume, automatically directs the midstream flow to smaller sample compartments to provide individual test samples.

U.S. Pat. No. 4,388,922 discloses a system for the automatic serial collection of body fluids in vacuum or suction canisters. The system utilizes serially connected canisters, but is intended for use during surgical procedures to facilitate the drainage of body fluids in relatively high volumes.

None of the prior art nor the specific methods in present use address the problems which currently exist in the serial collection of naturally voided urine specimens to monitor post-surgery clarity and color. There is, therefore, a need for a means to facilitate sample collection which is accurate, safe and sanitary, and yet is relatively simple and easy to use.

SUMMARY OF THE INVENTION

The present invention addresses and overcomes the problems and deficiencies in the prior art with a collecting and storage device for serially collected urine samples which includes a unitary main sample container having a plurality of separate serially arranged compartments for the receipt of serial urine samples. Each of the compartments has a transparent side wall to allow the visual observation of the sample for color and clarity. Each compartment has an inlet opening at the top for receipt of the sample and outlet opening at the bottom for discharge of the sample. Each inlet opening is provided with a suitable cover to enclose the sample contained in the compartment to prevent spillage, contamination and odor. The outlet from each compartment is provided with a valve to pass excess volume not needed for the sample or to discharge the sample when no longer needed.

The device of the present invention also utilizes visual indicia on each compartment to indicate the relative time of receipt therein of one of several serial urine samples. More specifically, the visual indicia is adapted to indicate the time of receipt of the sample relative to that of a sample in another compartment or relative to the time of receipt of serial samples in all other compartments.

Two or more types of visual indicia for establishing and maintaining the proper timed sequence of the samples may be used. The indicia may thus comprise a human readable message which is manually operable to indicate the proper timed sequence of the samples in the various compartments. Color coded indicia may also be used in lieu of or as a supplement to the human readable indicia.

The main container preferably includes three compartments which are disposed in side by side relation and are of generally rectangular horizontal cross section. The unitary container is constructed such that adjacent compartments have a common side wall. The transparent side walls of the compartments preferably comprise a common front wall of the container and the transparent wall on each compartment includes a scale indicating the level of the urine sample container therein which is graduated to indicate the volume of liquid contained in the compartment.

To facilitate pouring a urine sample into a compartment, each compartment may include an integral funnel overlying the inlet opening. The cover for the inlet opening may comprise an integral hinged lid at the top of each funnel. The funnels may also be integrally attached at their adjacent upper edges.

The device preferably also includes a main storage reservoir which is adapted to be hung below the main sample container and to be connected to the outlet openings of the various compartments such that the urine samples discharged from the compartments may flow by gravity into the common storage reservoir. The storage reservoir is preferably a flexible plastic bag and is connected to the compartments with a flexible plastic tube having a single inlet connection to the bag and a branched upper end for connection to the outlets of the compartments. Flow from each compartment into the connecting tube is controlled with an appropriate valve or clamp.

The upper container and attached lower reservoir are each adapted to be attached by separate anchor hooks to appropriate supporting structure.

BRIEF DESRIPTION OF THE DRAWINGS

DETAILED DESCRIPTION OF THE PREFERRED EMBODIMENT

Figure 1:
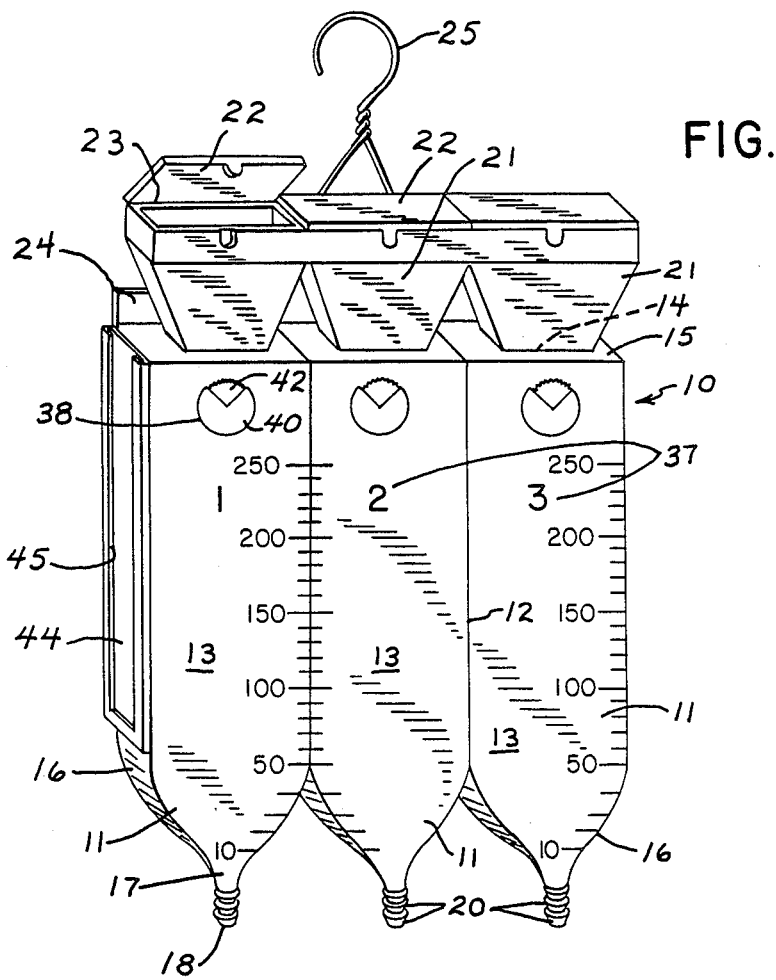
FIG. 1 is a front elevation, in perspective, of the main unitary container portion of the serial collection device of the present invention.
Figure 3:
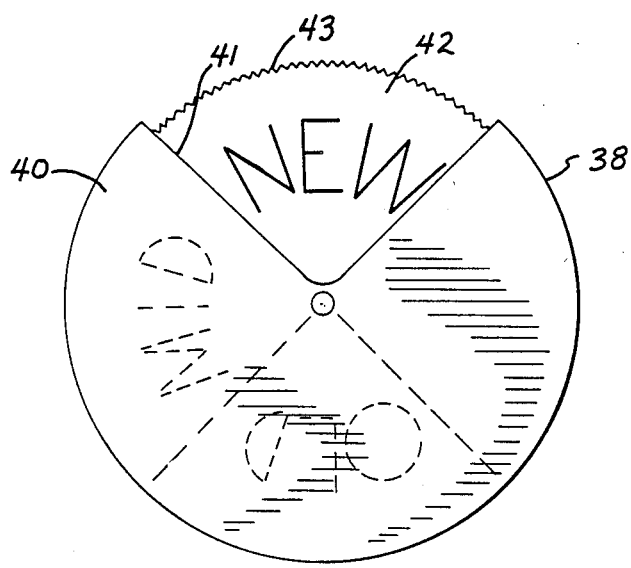
FIG. 3 is an enlarged view of the manually operable visual indicator for indicating relative timed receipt of the samples.

Referring initially to FIG. 1, the serial collection device of the present invention includes a unitary container 10 which comprises three integrally attached and serially arranged compartments 11. The container 10 is preferably of molded plastic construction and has an overall horizontal cross section of a generally rectangular shape. Thus, each of the integral compartments 11 has a shape which is also rectangular in horizontal cross section. The center compartment 11 shares a common side wall 12 with each adjacent end compartment. The face of the container 10 and, therefore, the front wall 13 of each compartment is transparent to allow visual inspection of the urine sample therein, as will be described hereafter in greater detail.

Each compartment has an inlet opening 14 in the top surface 15. Each compartment also includes a tapered lower portion 16 which terminates in a neck 17 defining an outlet opening 18. The neck 17 may be provided with a series of circumferential ribs 20 to help retain an outlet tube which may be attached thereto as will be described.

Each of the compartments 11 also preferably includes an integral funnel 21 forming an upwardly opening extension of the inlet opening 14. The wider open upward end of each funnel 21 is provided with a closable cover 22 including a hinge 23 integrally attaching the cover to the rear upper edge of the funnel 21. The rear wall of the container 10 includes an integral upwardly extending flange 24 which provides a surface for the attachment of a hook 25 or other convenient means for demountably hanging the container on a support.

Figure 2:
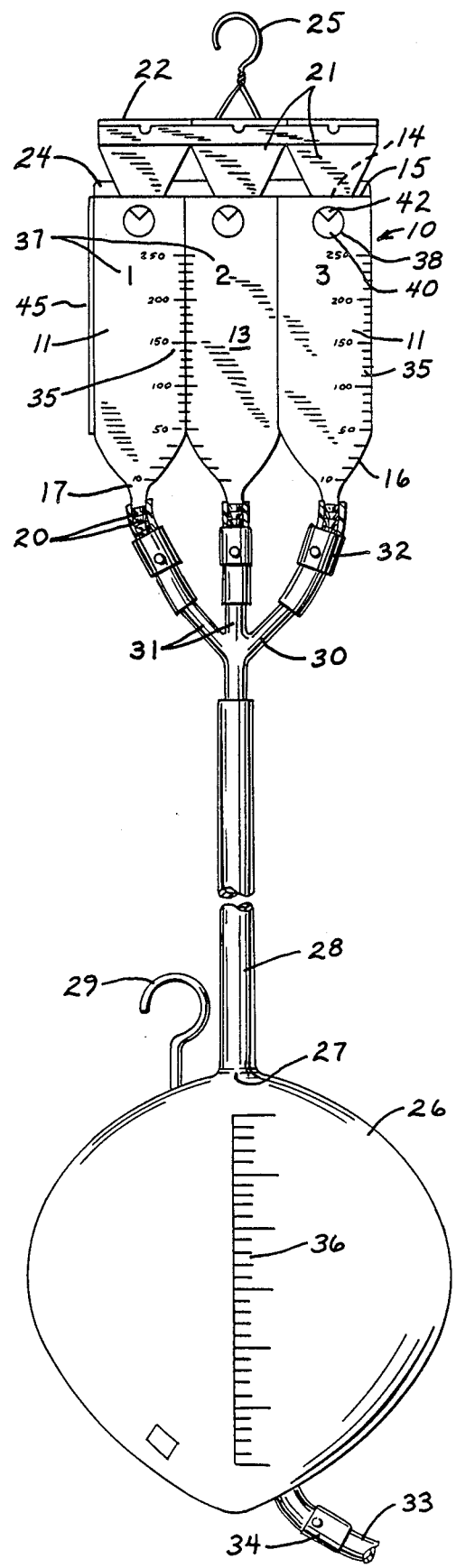
FIG. 2 is a front elevation view of the device including the lower storage reservoir and the tubular connection between the upper and lower units.

Referring also to FIG. 2, the serial collection device of the present invention may also include a stsorage reservoir 26 adapted to be disposed below the container 10 and to receive by gravity flow the urine selectively discharged from the compartments 11. The reservoir 26 comprises a flexible plastic bag having a volume substantially greater than that of the combined volume of the three compartments 11. An upper inlet 27 is defined by a flexible tube 28 including a branched upper end 30 defining tubular portions 31 for attachment to the neck 17 of the compartments. Each tubular portion 31 is provided with a valve or flow control clamp 32 just below its connection to the outlet opening 18 defined by the neck 17. The lower end of the reservoir 26 is provided with an oulet tube 33 including an appropriate control clamp 34. Separate support of the lower reservoir 26 is provided by a suitable hook 29 attached to the upper part of the rear wall.

The transparent front wall 13 of each compartment 11 includes a level scale 35 which is suitably graduated to indicate the volume of urine or other liquid contained in the compartment. Similarly, at least the front face of the lower storage reservoir 26 is transparent and includes a suitable scale 36 to provide a visual indication of the volume of urine stored therein.

To keep track of the order of the voidings of urine after removal of the catheter, in order that improvement in urine color and clarity may be assessed, the relative order of the voidings must be maintained. One or more means of providing a visual indication of the chronological order of the samples in the compartments may be used. One such means is to simply number the compartments from left to right with the numbers 1 through 3 as indicated at 37. However, such a numbering system is obviously inadequate and may result in confusion and loss of order for samples of the fourth and subsequent voidings during any particular period of monitoring. Thus, each compartment 11 is also preferably provided with a manually operable indicator 38 by which the relative time of the urine sample in that compartment may be identified with respect to the samples in the other two compartments. The indicator 38 comprises a raised circular slot 40 having an open upper sector 41. A circular thumb wheel 42 having a serated edge 43 is mounted for rotation in the slot 40. The thumb wheel 42 contains appropriate visual indicia which may be used to identify the relative time of the urine sample in the compartment, such as the words "NEW", "MID", and "OLD" printed within a quarter sector of the thumb wheel 42. The thumb wheel 42 may be manually operated to display one of the words in the open upper sector 41 or to display the blank quarter sector, as may be appropriate. In addition, the face of the circular slots 40 may each be provided with a different color to also help distinguish between or to recall the timing of a sample, as will be described.

The following procedure, outlining the manner in which the serial collection device of the present invention is utilized may be followed by an ambulatory and alert patient, after appropriate instruction, or by the nursing staff attending the patient. After the catheter is removed from the patient, the patient is provided with a conventional urinal or other appropriate receptacle and instructed to collect the initial and each subsequent voiding for sampling and monitoring. After opening the cover 22, the urine from the first voiding is poured into compartment number 1 which may typically have a capacity of 250 cc. Any excess volume is allowed to flow into the lower reservoir 26 by opening the flow control clamp 22 at the bottom of the compartment. The thumb wheel 42 on the manual indicator 38 is turned until the word "NEW" appears in the open upper sector 41. The second voiding of urine is collected in a similar manner, poured into the number 2 compartment 11 and the number 2 indicator 38 set such that the word "NEW" appears. The thumb wheel on the number 1 indicator is turned until the word "OLD" appears at the open upper portion. In a similar manner, the third voiding is poured into the number 3 compartment (with any volume in excess of approximately 250 cc drained into the reservoir 26) and the manual indicator 38 set to show the word "NEW". The indicator on the number 2 cup is changed to show "MID", thereby providing an immediate visual indication of the sequential order of the three samples.

There may typically be a span of 30 minutes to 4 hours between voidings and, therefore, a need for more than 3 samples during a typical shift. Therefore, the fourth voiding is poured into the number 1 compartment, after it has first been emptied into the reservoir 26 by opening the flow control clamp 32. The thumb wheel 42 on the number 1 compartment is then changed to identify the fourth sample as "NEW", and the indicators on the second and third compartments are turned to indicate "OLD" and "MID", respectively. The routine is repeated for successive voidings and samples from as many as three successive voidings are available for visual analysis to determine relative improvements in color and clarity. Serial urine collection until the proper clarity is obtained might typically require two to six days. In order to provide the basis for continuous assessment of progress, the main storage reservoir 26 may be emptied via the outlet tube 33 at the end of each work shift, leaving the previously collected serial samples in the compartments 11. The nursing staff on the succeeding shift will then have a baseline indication of urine color and clarity to begin their shift.

The side wall 44 of one of the compartments 11 may be provided with a means for holding a record card on which the nursing staff can provide more detailed data concerning the serial urine collection procedure. The holding device might comprise an integral transparent plastic pocket or slot 45 into which a data card may be slid or any other convenient supporting means. The supplemental data recorded on such a card may include the date, time, total volume and relative color of each urine voiding.

A single device of the present invention may be used by a patient during the patient's full term of hospitalization. The apparatus is easily disassembled for periodic rinsing or cleaning.

Use of the serial urine collection and storage device of the present invention, as hereinabove described, provides significant benefits over the apparatus and methods in present use. The device improves substantially the integrity of the serial collection procedure by reducing the chance of loss or misordering of a sample by accident or mistake. The manually operable indicator provides a positive means of identifying the relative order in which the voided samples were taken and may be utilized by an ambulatory and alert patient, as well as by the nursing staff. Should a patient inadvertently fail to properly set an indicator, the number and/or color code of the compartment used might at least be remembered by the patient so the proper sequence can be maintained. The closable covers on each of the compartments not only reduce the chance of spillage, but they also help eliminate the unpleasant urine odor in the patient's environment. The ability to direct any volume of urine in excess of that needed to fill a sample compartment to the storage reservoir is provided with substantially less direct handling than with present methods. This is particularly important in view of the concern over diseases transmissible through body fluids. The use of the main storage reservoir also provides the ability to assess overall urine color and total volume over a particular time period, such as a work shift. The device may be conveniently hung at the patient's bedside, in a wash room, or on any other suitable supporting structure. All of the foregoing benefits provide a general improvement in a routine which is not particularly appealing to the nursing staff.

I claim:

1. A collecting and storage device for visual analysis of serially collected urine samples, said device comprising:
   a unitary container having a plurality of separate, serially arranged compartments;
   each of said compartments having a transparent side wall, an inlet opening at the top for receipt of a urine sample, and an outlet opening at the bottom for the discharge of the urine sample;
   cover means on each compartment for selectively opening and closing the inlet opening; and,
   valve means on each compartment for selectively opening and closing the outlet opening.

2. The invention as set forth in claim 1 including visual indicia on each compartment for indicating the relative time of receipt of the urine sample therein.

3. The invention as set forth in claim 2 wherein said visual indicia is adapted to indicate the time of receipt of the sample relative to the time of receipt of a sample in another compartment.

4. The invention as set forth in claim 2 wherein said visual indicia is adapted to indicate the time of receipt of the sample relative to the time of receipt of the samples in all other compartments.

5. The invention as set forth in claim 2 wherein said visual indicia comprises two independent types of indicia on each compartment.

6. The invention as set forth in claim 5 wherein said indicia comprises a human readable type and a color coded type.

7. The invention as set forth in claim 6 wherein one of said indicia types is manually operable.

8. The invention as set forth in claim 1 wherein the container has three compartments disposed in side-by-side relation.

9. The invention as set forth in claim 8 wherein the compartments are of generally rectangular horizontal cross section.

10. The invention as set forth in claim 9 wherein adjacent compartments share a common side wall.

11. The invention as set forth in claim 1 including a main storage reservoir disposed below the container, said reservoir having fluid connection means to the outlet openings of the compartments for the selective receipt of urine discharged by gravity flow therefrom.

12. The invention as set forth in claim 11 wherein the storage reservoir comprises a flexible plastic bag and the fluid connection means comprises a flexible plastic tube having a lower end in fluid communication with the reservoir and a branched upper end providing attachment to each of the outlet openings.

13. The invention as set forth in claim 12 wherein the attachment to each of the outlet openings is demountable.

14. The invention as set forth in claim 12 wherein the attachment to each of the outlet openings includes a flow control means for the selective control of discharge from each compartment.

15. The invention as set forth in claim 11 including hanger means for attaching the device to a support structure.

16. The invention as set forth in claim 15 wherein said hanger means comprises an anchor hook attached to each of the container and the reservoir.

17. The invention as set forth in claim 1 wherein the transparent side wall of each compartment includes a urine level scale graduated to indicate the volume of urine in the compartment.

18. The invention as set forth in claim 1 whrein each inlet opening includes an integral funnel and the cover means comprises an integral hinged lid for each funnel.

19. The invention as set forth in claim 18 wherein the funnels are attached at their adjacent upper edges.

* * * * *